United States Patent [19]

Katz et al.

[11] 4,154,114

[45] May 15, 1979

[54] BIOMETRIC MEASURING DEVICE

[75] Inventors: Louis Katz, Flushing; Werner Gruenebaum, Monsey, both of N.Y.

[73] Assignee: Sonometrics Systems, Inc., New York, N.Y.

[21] Appl. No.: 856,961

[22] Filed: Dec. 2, 1977

[51] Int. Cl.² ........................................... G01N 29/00
[52] U.S. Cl. ...................................... 73/629; 128/660; 128/774
[58] Field of Search ................. 73/596, 597, 606, 609, 73/610, 612, 614, 615, 627, 629, 632; 128/2 V, 2.05 Z

[56] References Cited

U.S. PATENT DOCUMENTS

| 3,792,613 | 2/1974 | Couture | 73/610 |
| 3,808,879 | 5/1974 | Rogers | 73/609 |
| 3,821,891 | 7/1974 | Collins et al. | 73/612 |
| 4,033,177 | 7/1977 | Case | 73/614 |

Primary Examiner—Stephen A. Kreitman
Attorney, Agent, or Firm—McAulay, Fields, Fisher & Goldstein

[57] ABSTRACT

A biometric measuring device measures distances between selected elements in a human body, and in particular, the human eye. Trace means produces respective signals for a preselected number of cycles wherein each signal represents the distance between the selected elements that is to be measured. Converting means averages the respective signals over the preselected number of cycles to produce a distance signal representing the distance between the selected elements of the body. Display means displays this distance signal as a number.

14 Claims, 7 Drawing Figures

BIOMETRIC MEASURING DEVICE 10

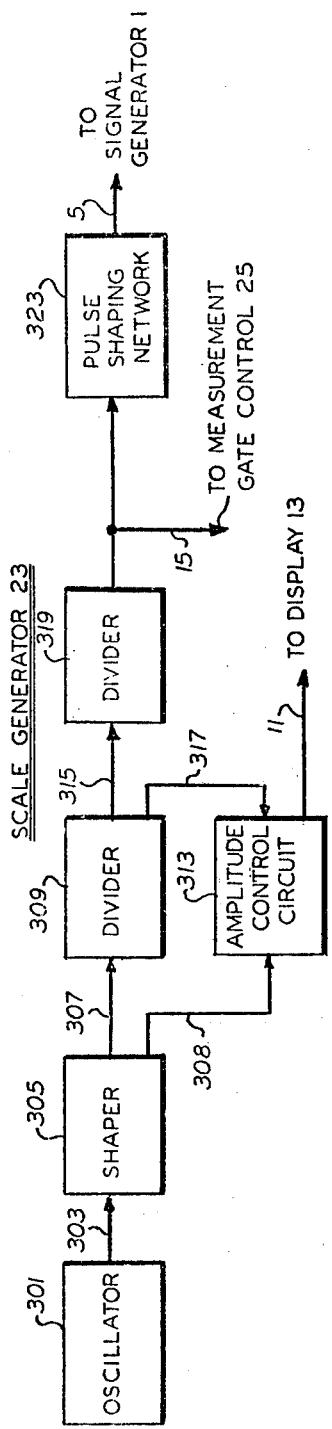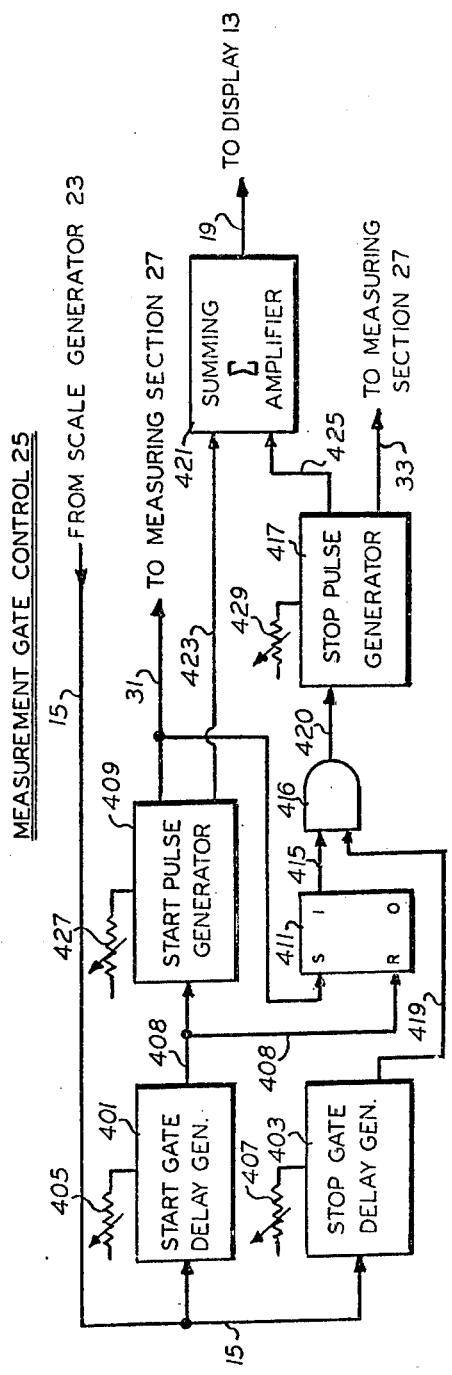

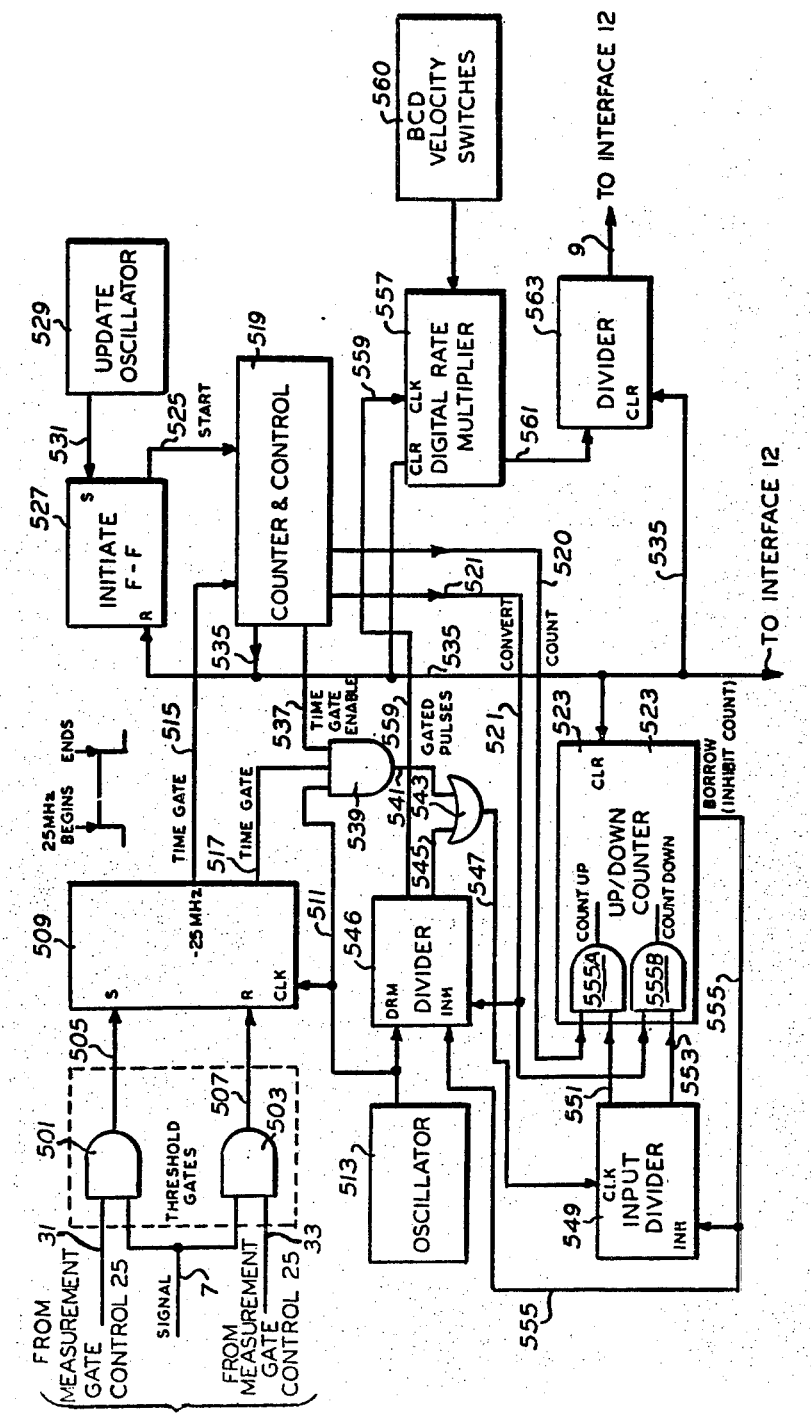

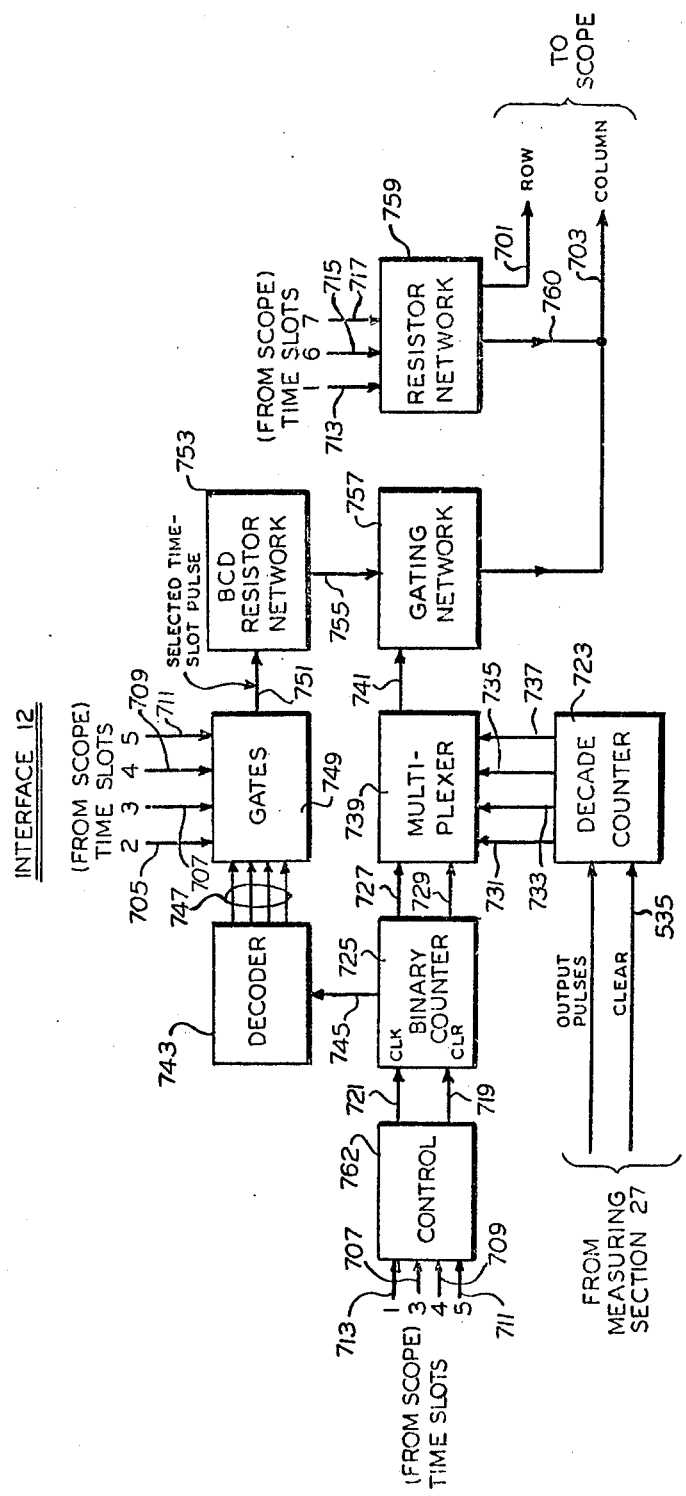

BIOMETRIC MEASURING DEVICE

BACKGROUND OF THE INVENTION

This invention pertains to improvements in biometric measuring devices, and particularly those devices which are adapted to measure the distance between selected elements in the human body. The preferred embodiment of the present invention is especially well suited to measure the distance between selected elements in the human eye and will be described in this environment.

Biometric measuring devices have heretofore been utilized to measure distances between elements in, for example, the eye. They have been described in the literature and the following articles disclose devices presently describing the state of the art: "Transducer Alignment and Electronic Measurement of Visual Axis Dimensions in the Human Eye Using Time-Amplitude Ultra-Sound" by D. J. Coleman and B. Carlin, Ultrasonics in Ophthalmology, Symposium Munster, August 1966, pp. 207-217; "A New System for Visual Axis Measurement in the Human Eye Using Ultra-Sound," D. Jackson Coleman and Benson Carlin, Archives of Ophthalmology, January 1967, Vol. 77, pp. 124-127; and "Ophthalmic Biometry Using Ultrasound", D. Jackson Coleman, International Ophth. Clin., Vol. 9, pp. 667-683, 1969.

The latter article describes a device typical of the prior art. A transducer produces a narrow beam of ultrasonic energy which is directed axially into the human eye. Part of this ultrasonic signal is reflected from the interfaces between various elements comprising the eye structure. These reflected signals or "echoes" are received by the transducer, which converts the echoes into appropriate electrical signals. The elapsed time between the echoes is proportional to the distance between the elements from which the respective echoes are reflected. These signals are then applied to both an oscilloscope display and an electronic interval counter. The electronic interval counter is triggered to start and stop counting by means of moveable "gates" shown on the oscilloscope display so that the time between receipt of signals from desired eye elements may be determined. This time interval is then converted into an appropriate distance measurement.

However, serious drawbacks are associated with the above type of construction. For example, these are "one-shot" devices that produce a distance measurement based on only one ultrasonic pulse. This is a highly inaccurate measurement and, in a number of cases, produces results that are unacceptable for biometric measurement.

An even greater problem is due to the fact that the sound waves travel through the different elements comprising the eye structure at respectively different velocities depending upon the sound-carrying capabilities of the medium. However, these prior art devices are incapable of compensating for these velocity variations and the measurements are therefore based upon an assumed constant velocity of sound through the different media comprising the eye structure. Thus, the measurements produced by these devices are, at best, an approximation of the true distances and therefore may actually render the measurement completely useless for its intended use.

Accordingly, it is an object of the present invention to provide an improved biometric measuring device for measuring distances between selected elements of the human body.

It is also an object of the present invention to provide such a device that is particularly well suited for measurement of distances between selected elements in the human eye.

A further object of this invention is to provide a device of the type described that measures such distances over a predetermined number of cycles and averages those distances to obtain a single distance thereby producing an extremely accurate reading.

Another object of the present invention is to provide an economical biometric measuring device without sacrificing accuracy or ease of operation.

A further object of another aspect of the invention is to provide a biometric measuring device of the type described wherein the velocity of the sound signal in the particular medium is automatically taken into consideration in measuring distances.

A more specific object of this aspect of the invention resides in the novel details of circuitry that provide a biometric measuring device of the type described wherein the device is pre-programmed to compensate for the velocity of sound in the particular medium under consideration to provide highly accurate distance measurements.

SUMMARY OF THE INVENTION

The present invention comprises a biometric measuring device for measuring distances between selected elements in the human body and, in particular, for measuring distances between elements comprising the eye structure. A trace means is provided for producing timed sequence signals representing the distance between the elements for each cycle of operation of said trace means. Converting means, responsive to said timed sequence signals, converts said signals into distance signals representing the distance between said selected elements and average said distance signals over a predetermined number of cycles of said trace means. Display means respond to said average distance signal for displaying the distance between the selected elements of the human body.

BRIEF DESCRIPTION OF THE DRAWINGS

Other features and advantages of the present invention will become more apparent from a consideration of the following detailed description when taken in conjunction with the accompanying drawings, in which:

FIG. 3 is a schematic circuit wiring diagram, in block form, of the scale generator portion of the circuit shown in FIG. 1;

FIG. 4 is a schematic circuit wiring diagram, in block form, of the measurement gate control portion of the circuit shown in FIG. 1;

FIG. 5 is a schematic circuit wiring diagram, in block form, of the measuring portion of the circuit shown in FIG. 1;

FIG. 7 is a schemati- circuit wiring diagram of the interface portion of the circuit shown in FIG. 1.

DETAILED DESCRIPTION OF THE PREFERRED EMBODIMENT

Figure 1:
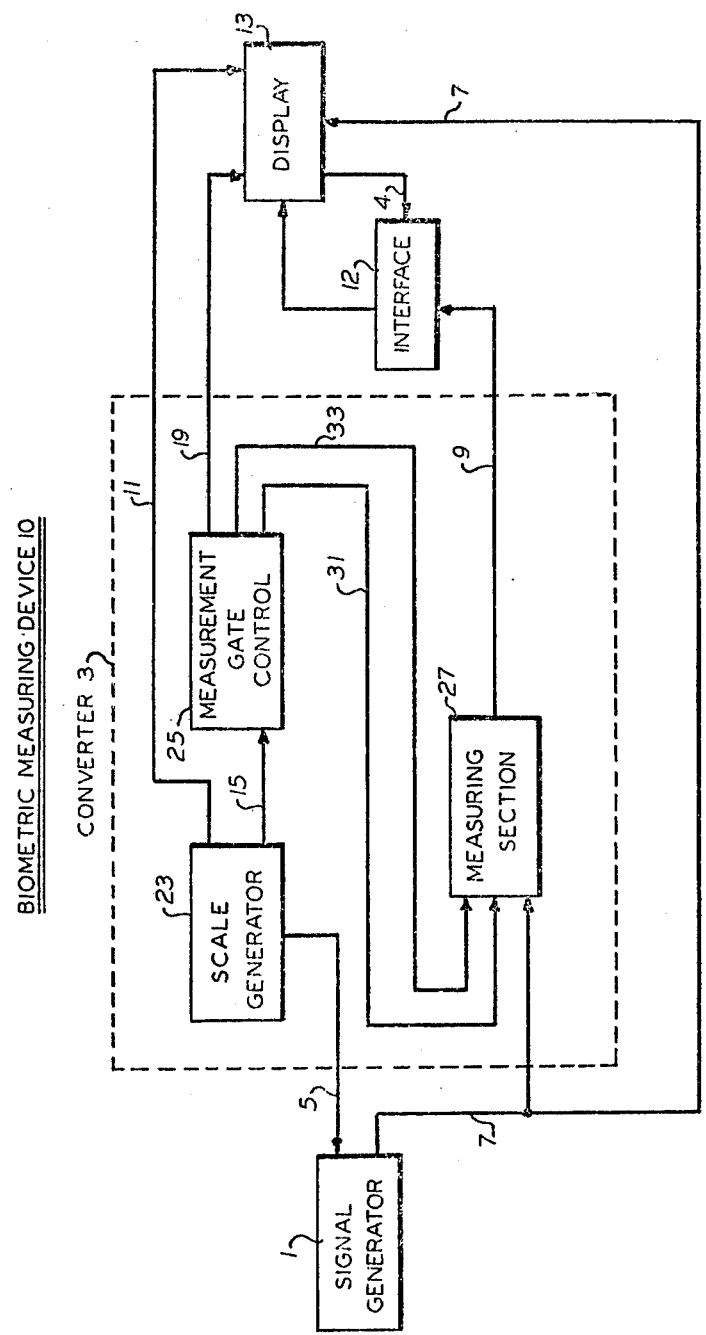
FIG. 1 is a schematic circuit wiring diagram, in block form, of a biometric measuring device constructed according to the present invention.

A biometric measuring device constructed according to the present invention is designated generally by the reference numeral 10 in FIG. 1. A primary application of the present invention is in ophthalmic biometry and, specifically, ultrasonic biometry in the A-mode or time-amplitude ultrasonography for measurements along the visual axis of the human eye. For that reason, the operation of the invention is described in conjunction with measurements of the distance between selected elements comprising the structure of a human eye. However, this is for illustrative purposes only and is not to be interpreted as being a limitation of the present invention.

The device or apparatus 10 comprises a signal generator 1 that produces a plurality of timed pulses. The particular construction of signal generator 1 is conventional. That is, the signal generator generally comprises a transducer for converting electrical energy into sound waves (hereinafter "trace signals"). (In practice, it has been found that a transducer comprising a crystal resonating at approximately 1KHz provides the best transmission and echo wave characteristics for measurement of the linear dimensions of the human eye.) The sound waves are directed at the parts of the body to be measured or, in this case, at the eye. Usually a single sound wave is emitted in response to a single pulse. However, when the wave impinges on an element or an interface between elements, a portion of the wave is reflected or an echo is produced. Since the eye is composed of many such elements (i.e., cornea, lens, etc.) many such echoes are produced for each emitted sound wave. The series of echoes are received at the signal generator 1 at different times related to the different distances the sound waves had to traverse. The echoes are detected by a receiver that forms a portion of the signal generator.

More specifically, the receiver portion of signal generator 1 converts the echo signals into corresponding electrical signals that occur in timed sequence depending on the time required for the sound waves to reach a target and return. The time difference between these echo signals is proportional to the distance between the elements of the eye. Generally, the same transducer is used both for receiving and transmitting. More specific information on a signal generator of the type under consideration may be had by reference to the aforementioned article by D. Jackson Coleman, entitled "Ophthalmic Biometry Using Ultrasound."

As shown in FIG. 1, the present invention also includes a converter 3 for converting the plurality of electrical signals into corresponding distances and for averaging these distance measurements over a number of cycles to produce highly accurate results. To be more specific converter 3 provides a signal on a lead 5 that triggers signal generator 1 to produce the initial sound wave. Converter 3 also accepts from signal generator 1, on a lead 7, the series of electrical signals produced by the echo signals from the interfaces between the elements of the eye.

Figure 2:
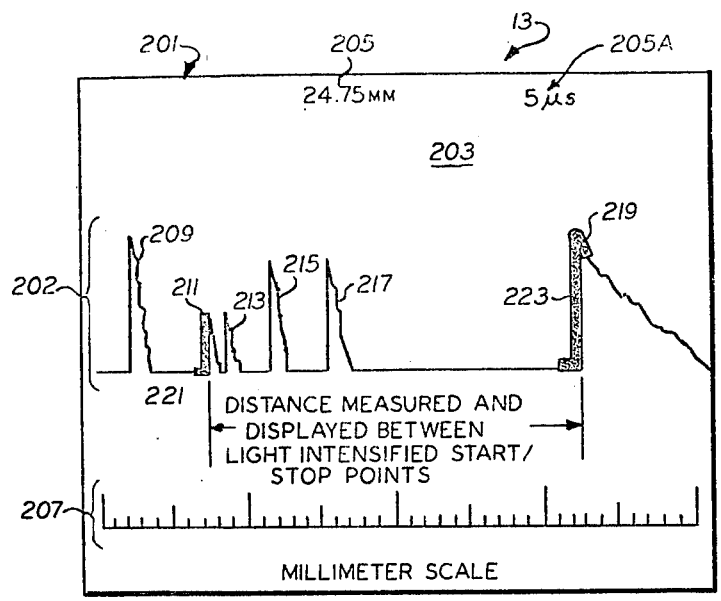
FIG. 2 is a graphical representation of the display produced by the display portion of the circuit of FIG. 1.

Converter 3 comprises a scale generator 23 for generating timed signals on a lead 11. Converter 3 also comprises measurement gate control 25, the input terminals of which are connected by the lead 15 to the output terminals of scale generator 23. The gate control 25 is operable to produce measurement gate start and stop signals on respective leads 31 and 33, as noted in greater detail below. Converter 3 further comprises a measuring section 27, which receives, at its input terminals via lead 7, the series of electric signals from generator 1, and the start and stop signals from gate control 25. The measurement section 27 is operable to produce on a lead 9, distance signals that represent the distance between selected elements of the eye. The lead 7 is connected to display 13. Similarly the lead 9 is connected through an interface 12 to display 13. Additionally, the display 13 is connected, by a lead 19 to output terminals of the gate control 25 and, by a lead 11, to scale generator 23. The display contains a screen that displays the echo signals along an axis such that the distance between displayed signals is related to the distance between elements by a scale factor. Scale generator 23, measurement gate control 25, and measuring section 27 are more fully shown in FIGS. 3, 4 and 5, respectively and described in greater detail below. The screen portion of display 13 is illustrated in FIG. 2.

Display 13 comprises a screen 201 that produces a numeric display representing the distance between selected elements of the eye, and a graphical display of all sound signals. Additionally a scale 207 is also produced on the screen. FIG. 2 is an illustration of the visual portion of display 13 as seen during a typical cycle of operation when measuring the distance between elements in a human eye. The screen 201 visually displays the signals from converter 3 and signal generator 1. In practice the screen 201 is the viewing face of an oscilloscope (not shown) having a cathode-ray tube (CRT) 203. The oscilloscope is of the type which is operable to diplay wave trains on channels 202 and 207 as well as an alphanumeric display 205. In addition, the oscilloscope may permit examination of a waveform on an expanded scale as indicated by time base indicator 205A. For example, the oscilloscope may comprise Tektronix oscilloscope Model No. 5403 manufactured by Tektronix, Inc. of Beaverton, Oreg.

Channel 202 displays a series of signals shown as pulses 209, 211, 213, 215, 217 and 219, corresponding to the signals appearing on lead 7 from the signal generator 1. It also displays the measurement gate start and stop signals, shown as intensified pulses 221 and 223, respectively, that appear on lead 19 from measurement gate control 25. The channel 207 displays the signals on lead 11 from scale generator 23 as a series of scale markers.

The alphanumeric display 205 visually displays a number representing the distance between the preselected elements of the eye and letters representing the units. An interface 12 is connected between the measuring section 27 and the circuitry controlling the display 205 to convert the signals from the section 27 into signals that are compatible for use in the display 205 circuitry. Timing signals for interface 12 are obtained via a lead 4 from display 13.

The first pulse, pulse 209 in channel 202, is colloquially referred to as the "transducer main bang." That is, pulse 209 is the initial sound pulse (trace signal) emitted by the transducer in response to the energizing pulse appearing on lead 5. Pulses 211, 213, 215, 217 and 219 are the echo pulses. That is, the pulses represent that part of the energy from the "main bang" pulse that is reflected from the interfaces between the various elements of the eye. In practice, these pulses are associated as follows with the various interfaces between the parts of the eye: pulse 211 is representative of the echo produced by the anterior surface of the cornea; pulse 213 is representative of the echo produced by the posterior surface of the cornea; pulse 215 is representative of the echo produced by the anterior surface of the lens; pulse 217 is representative of the echo produced by the posterior surface of the lens; and pulse 219 represents the echo produced by the retina.

As noted above, the intensified pulses 221 and 223 are the visual representations of the opening and closing of the distance measurement gate. The length between these intensified segments represents the time during which the converter 3 is operable to calculate the distances between eye elements. In operation, the distance between the leading edge of the first pulse in the group of pulses associated with the intensified segments will be measured since this distance represents the distance between the corresponding eye elements.

FIG. 2 is not necessarily to scale since there is a substantial time delay between the transducer main bang pulse and the first echo pulse 211. In order to display all pulses (i.e., from 209 to 219) a compressed time base scale would have to be used. However, when it is desirable to examine only the echo pulses (i.e., pulses 211–219) an expanded time base scale may be used. This is a conventional control on oscilloscopes such as the type identified above.

Scale Generator 23

As shown in FIG. 3, scale generator 23 comprises an oscillator 301. Although any frequency could be selected in accordance with principles of this invention, the preferred embodiment utilizes an oscillator having a frequency of 766 kilohertz for reasons which will become apparent from a consideration of the description hereinbelow. The output terminals of oscillator 301 are connected to a pulse shaper 305 by a lead 303. The shaper is a monostable multivibrator or "one-shot," which produces a pulse having a preselected width on every positive excursion of the signal on lead 303. The output pulses of shaper 305 are applied by a lead 307 to a divider 309 and by a lead 308, to an amplitude control circuit 313. The output terminals of the amplitude control circuit 313 are connected by the lead 11 to the display 13. Amplitude control circuit 313 is more fully shown in FIG. 6 and described below.

Divider 309 divides the signal at its input by a factor of 10. In practice, the divider 309 may comprise a four-stage counter which is pre-loaded to start from a count of 6. When divider 309 recycles from 15 to the pre-loaded count of 6 it produces a transition which forms the output signal on output lead 315 which is connected to divider 319. Thus, the circuit 309 produces one signal on output lead 315 for every ten signals on input lead 307. Divider 309 also provides signals to control 313 via a cable 317 comprising a plurality of leads.

The output terminals of the divider 319 are connected by the lead 15 to a pulse shaping network 323. The divider 319 is operable to divide the pulses on lead 315 by a factor of 64. That is, for every 64 pulses appearing on the lead 315, one pulse will appear on the lead 15. Since, as noted above, the oscillator 301 produces a 766 KHz signal, the frequency of the signal on lead 315 will be 76.6 KHz, and the frequency of the signal on lead 15 will be 1.2 KHz. As noted above (FIG. 1), lead 15 is connected to measurement gate control 25.

It is highly desirable that the pulse applied to trigger signal generator 1 be as narrow as possible. Accordingly, the pulse shaping network 323 may comprise a differentiator that produces a so-called spike pulse. The output terminals of the network 323 are connected to the signal generator 1 by the lead 5.

Amplitude Control Circuit 313

Amplitude control circuit 313 generates signals having varying amplitudes. These signals are applied to display 13 via the lead 11 and appear as a series of scale markers or graduations in channel 207 (FIG. 2). Amplitude control circuit 313 produces markers having three amplitudes: a large amplitude marker every 10th graduation; a medium amplitude marker every 5th graduation; and a small amplitude marker for the remaining graduations.

Figure 6:
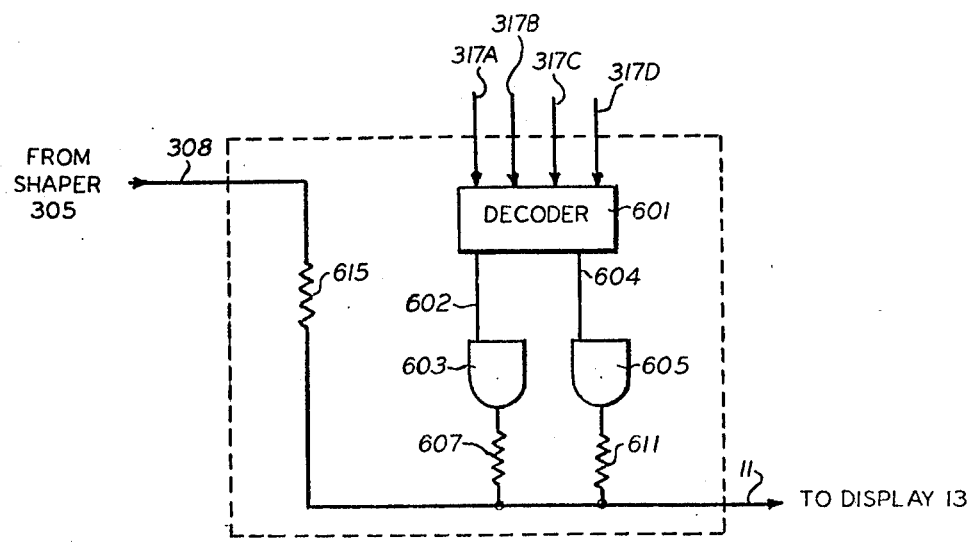
FIG. 6 is a schematic circuit wiring diagram of the amplitude control portion of the present invention.

More specifically, as shown in FIG. 6, cable 317 from divider 309, comprising leads 317A–317D, applies signals from divider 309 to a decoder 601. Output leads 602 and 604 of decoder 601 are connected to respective input terminals of NAND gates 603 and 605.

The output terminals of gate 603 are connected to lead 11 through a resistor 607. Similarly, the output terminals of gate 605 are connected to lead 11 through a resistor 611. When a respective gate is in the closed state, the associated resistor is grounded.

As noted above, the lead 308 from shaper 305 is also connected to amplitude control circuit 313. Lead 308 is connected to one terminal of a resistor 615, the other terminal of which is connected to the common terminals of resistors 607 and 611 and the lead 11.

The leads 317A–317D are connected to the respective stages of the four-stage counter comprising the divider 309. Thus, each count will be applied to the decoder 601. The logic of decoder 601 is such that gate 303 is opened for each fifth count and gate 605 is opened for each tenth count. Thus, under normal operation the resistors 607 and 611 will be connected to ground through the respective closed gates. The pulse applied to lead 308 from shaper 305 will therefore be attenuated by the reistors 607 and 611 to produce a low amplitude signal on lead 11. This will result in a small scale marker being displayed on screen 201.

However, on the fifth count, gate 603 opens so only resistor 611 is connected to ground. Thus, the amount of attenuation decreases and the amplitude of the scale marker is increased, as shown in FIG. 2. On a tenth count, both gates 603 and 605 open thereby eliminating attenuation by resistors 607 and 611 to produce a large amplitude scale marker.

Measurement Gate Control 25

FIG. 4 illustrates the measurement gate control 25 for producing distance measurement gate start and gate stop signals so that the distance between the selected elements of the eye may be measured. As will become evident, adjusting the position of the aforementioned start and stop signals to overlap the desired elements (pulses 221 and 223 in FIG. 2) automatically selects the elements between which the distance is to be measured.

The signal on lead 15 (from scale generator 23) is applied to start gate delay generator 401 and stop gate delay generator 403. In the preferred embodiment, delay generators 401 and 403 are variable width monostable multivibrators. The width of the output pulses from generators 401 and 403 may be adjusted by variable resistors 405 and 407, respectively, in the conventional manner.

The generator 401 is connected by a lead 408 to a start pulse generator 409. The trailing edge of the pulses on output lead 408 triggers the start pulse generator 409.

Start pulse generator 409 may also be a monostable multivibrator, the width of whose output pulse (hereinafter "start pulse") is manually controlled as by a variable resistor 427 in the conventional manner.

The reset terminal R of a bistable multivibrator or flip-flop 411 is connected to the lead 408 and the clock input terminals are connected by lead 31 to the output terminals of start pulse generator 409. The flip-flop 411 is reset on the leading edge of a pulse from delay generator 401 and is set by the trailing edge of a pulse from start pulse generator 409. The "1" output terminal of flip-flop 411 is connected by a lead 415 to one input terminal of a NAND gate 416. The other input terminal of NAND gate 416 is connected by a lead 419 to the output terminal of stop gate delay generator 403. The output terminals of gate 416 are connected by a lead 420 to a stop pulse generator 417. Generator 417 is a monostable multivibrator that produces pulses the width of which may be varied manually by adjusting a variable resistor 429. NAND gate 416 is operable to produce a pulse when flip-flop 411 is set and when the output pulse on lead 419 returns to normal.

Output leads 423 and 425 from start pulse generator 409 and stop pulse generator 417, respectively, are connected to the input terminals of summing amplifier 421. The output terminals of amplifier 421 are connected by the lead 19 to the display 13. As noted above, the display 13 may comprise an oscilloscope, in which case the lead 19 is connected to the Z-axis input terminals. The signals on lead 19 produce the intensified distance measurement gate signals 221 and 223 on the screen or scope face.

The lead 31 connects the output terminals of the start pulse generator 409 to the measuring section 27. Similarly, the lead 33 connects the output terminals of the stop pulse generator to the measuring section.

The operation of the measurement gate control 25 is as follows. The leading edge of a pulse on lead 15 causes both start gate delay generator 401 and stop gate delay generator 403 to produce pulses on leads 408 and 419, respectively. Since the generators produce variable width pulses, the width of these pulses is preselected according to the requirements of the operator by selecting the proper values of the respective resistors 405 and 407.

The trailing edge of the pulse on lead 408 causes start pulse generator 409 to generate a start pulse, the width of which is similarly preselected by the value of resistor 427. Thus, a start pulse appears on lead 31 a predetermined time after the occurrance of the leading edge of the pulse on lead 15. This time is predetermined by the setting of variable resistor 405. The width of the start pulse on lead 31 is similarly preselected by variable resistor 427.

The trailing edge of the pulse produced by stop gate delay generator 403 causes stop pulse generator 417 to produce a pulse, the leading edge of which occurs a specified time after the leading edge of the pulse on lead 15. That is, the time interval between the leading edges of the pulses on leads 15 and 425 will be determined, in part, by the width of the pulse produced by stop gate delay generator 403.

Flip-flop 411, which can not be set until after a start pulse has been generated on lead 31, inhibits the possibility of a stop pulse on lead 33 occuring before a start pulse has been completed. That is, until flip-flop 411 is set, NAND gate 416 will not pass the triggering pulse from stop gate delay generator 403 to stop pulse generator 417.

Summing amplifier 421 produces a signal on lead 19 whenever a signal or start pulse appears on lead 423 from start pulse generator 409 or a stop pulse is generated by stop pulse generator 417 on the lead 425. Thus, a signal appears on lead 19 corresponding to a start signal on lead 31 and another signal appears on lead 19 corresponding to a stop signal on lead 33, causing pulses 221 and 223 to appear on screen 201.

Measuring Section 27

FIG. 5 illustrates the preferred embodiment of the measuring section 27. Leads 31 and 33 from measurement gate control 25 are connected to input terminals of NAND gates 501 and 503, respectively. The other common input terminal of gates 501 and 503 is connected to lead 7, which carries the output signal of signal generator 1.

Gates 501 and 503 are threshold gates. That is, when signals of at least a predetermined magnitude appear on both input leads to one of the threshold gates 501 or 503, an output signal will appear on the respective leads 505 and 507, which are connected to the output terminals of the associated gates. Connected to the leads 505 and 507 are the respective set and reset terminals S and R of a JK flip-flop 509. The clock input CLK of flip-flop 509 is supplied by lead 511 from an oscillator 513.

In effect, flip-flop 509 is controlled by the timed sequence trace signals from signal generator 1 via the lead 7. As is conventional in JK flip-flops, after a set pulse appears on line 505, upon the next clock pulse on lead 511, flip-flop 509 sets. When flip-flop 509 sets, a time gate pulse appears on leads 515 and 517, which are connected to the output terminals of flip-flop 509.

As will hereafter become clearer, counter and control 519 provides means for controlling the averaging functions of the present device. Lead 515 is connected to counter and control 519. In the preferred embodiment counter and control 519 is a six-stage counter with appropriate logic, which has the capability of counting to 64, for reasons which will become obvious hereinbelow. Counter and control 519 is incremented on the trailing edge of the pulses on lead 515, and therefore records the number of start - stop cycles which have activated flip-flop 509. That is, a pulse on lead 515 is initiated when the flip-flop is set and it terminates when the flip-flop is reset. Upon reaching the count of 64 or, in other words, after 64 cycles of start and stop pulses have elapsed, counter and control 519 produces an output pulse on lead 521. Lead 521 is connected to up/down counter 523. More specifically, up/down counter 523 is conventional. Lead 521 is connected to the count down control terminal of counter 523 and enables counter 523 to count down in response to a signal on lead 521.

Another input terminal of counter and control 519 is connected to lead 525 which, in turn is connected to an initiate flip-flop 527. Lead 525 provides the pulse for counter and control 519, which permits counter and control 519 to start counting the pulses appearing on lead 515. A variable frequency update oscillator 529, through lead 531, sets initiate flip-flop 527. Thus, upon a signal from update oscillator 529 counter and control 519 is enabled to start a counting cycle.

The counter and control performs a number of different control functions. Thus, upon receipt of a pulse from flip-flop 527, followed by the receipt of a pulse from flip-flop 509, counter and control 519 produces a reset or clear pulse on a lead 535. The lead 535 is connected to the reset terminal R of flip-flop 527 and immediately resets the same. The signal on the lead 535 also resets or clears counter 523. Also, upon receipt of the following pulse from flip-flop 509 in a cycle of operation, via the lead 515, a count signal is produced on the lead 520. The lead 520 is connected to the counter 523 and the signal appearing on lead 520 enables counter 523 to begin counting in the up direction.

A lead 537 connects counter and control 519 with a gate 539. Lead 537, together with a lead 517 from flip-flop 509 and the lead 511 from oscillator 513, carry input signals to coincidence or NAND gate 539. When flip-flop 509 is set and counter and control 519 is counting, the signals on lead 517 and 537 enable coincidence gate 534 to pass the pulses on lead 511 from oscillator 513 to the output terminals of the gate.

The output signal from coincidence gate 539 is applied, via a lead 541, to the input terminal of an NOR gate 543. The other input terminal to NOR gate 543 is connected by a lead 545 to an output terminal of digital rate multiplier ("DRM") divider 546. Normally, the signal on lead 545 is logically conditioned to permit the signals on lead 541 to pass through NOR gate 543 and appear on lead 547, connected to the output terminals thereof.

Lead 547 is connected to the clock terminals CLK of a divider 549, the output terminals of which are connected to the input terminals of the counter 523 by leads 551 and 553. In the preferred embodiment, divider 549 is a two-stage counter, which in effect divides the input signals on lead 547 by a factor of 4. Because of divider 549, up/down counter 523 stores only one-quarter of the pulses on lead 547 that occur between the first signals located in the start and stop pulses on leads 31 and 33. In the preferred embodiment up/down counter 523 comprises four suitably-ganged circuit chips, for example, Texas Instruments SN74193, to provide a 16-stage binary counter. These are driven through gates 555A and 555B to cause the counter to count up or down as the case may be.

As noted below, the present invention averages the measurements over a number of different cycles to provide highly accurate results. In the present embodiment, the measurements are averaged over 64 cycles. Thus, the counter and control unit 519 is adapted to count to 64 for each measurement cycle.

During the interval that counter and control 519 counts to 64, a pulse is produced on the lead 520 that enables counter 523 to count in the up direction. After counter and control 519 has accumulated a count of 64, it produces a signal on lead 521. This pulse conditions up/down counter 523 to commence counting down. It also sets DRM divider 546 to enable NOR gate 543 only every four cycles of oscillator 513, thus effectively reducing the frequency of oscillator 513 from 25 MHz to 6.25 MHz.

To be more specific, DRM divider 546 may comprise two ganged JK flip-flops which are normally inoperative in the absence of a signal on the lead 521. That is, the flip-flops normally produce an enabling signal on the lead 545 so that the pulses appearing on the lead 541 are gated through to divider 549. However, when the signal appears on lead 521, the flip-flops comprising the divider 546 are enabled so that effectively, the enabling signal on lead 545 occurs only on every fourth signal applied to the flip-flops. Thus, when counting down, the signal on the lead 547 is divided by a factor of four.

Upon reading a count of zero in the count-down mode, up/down counter 523 produces a burrow pulse on lead 555. Lead 555 applies the signal to an inhibit terminal INH of dividers 546 and 549 which are inhibited from generating any further clock pulses.

The present invention also provides velocity compensation so that an accurate result is produced by the present device. That is, the present device compensates for the velocity of the signal in the different mediums comprising the eye. The velocity compensation network includes digital rate multiplier (DRM) 557 which is clocked by signals on a lead 559 from DRM divider 546. These signals are only provided during the time that a convert signal appears on lead 521 (i.e., during the time that up/down counter 523 is counting down).

As noted above, pulses on lead 559 occur at one-quarter the frequency of oscillator 513. However, because of divider 549, up/down counter 523 is counting down at one-quarter of the rate of the pulses on leads 545 and 559. Thus, four times the number of pulses stored in up/down counter 523 appear on lead 559 before DRM divider 546 is inhibited. However, as previously explained, up/down counter 523 stores only one-quarter of the clock pulses that occurred between the 64 cycles of start and stop pulses. Therefore, the full total of oscillator pulses appear on lead 559 that oscillator 513 produced, but at one-quarter of the frequency.

This system permits the use of an economical state of the art DRM 557 without the loss of accuracy caused by a reduction in the pulse throughput which would result from a lower frequency oscillator 513.

Digital rate multiplier 557 is controlled by BCD velocity switches 560. Switches 560 in the illustrated embodiment may be three "thumbwheel" switches controlling DRM 557 in a BCD mode. For illustrative purposes, the DRM 557 may comprise four stages the first of which is a flip-flop. The succeeding three stages may comprise Texas Instruments rate multipliers type SN74167, each one of which is controlled by a respective one of the switches comprising 560. The flip-flop produces a BCD signal representing the most significant place and each of the three multipliers produces signals representing the next lower three significant places. The flip-flop, in conjunction with the multipliers effectively causes the number of pulses applied to DRM 557 to be multiplied by a factor of V/2000, where V is the velocity setting of the three switches comprising BCD velocity switches 560 and can vary between 1000 and 1999.

The output terminals of DRM 557 are connected by a lead 561 to the input terminals of a divider 563. Divider 563 in the preferred embodiment is a four-stage counter, which effectively divides the number of pulses appearing on input lead 561 by 16. The output terminals of the divider 563 are connected by a lead 9 to display means 13, and more particularly to the interface 12 for numeric display 205. Divider 563 is cleared at the beginning of a new accumulation cycle of 64 trace cycles by the reset pulse on lead 535.

Interface 12

Illustrated in FIG. 7 is the interface 12 that drives the circuitry for the display portion 205. As noted above, the present embodiment may use a Tektronix oscilloscope Model No. 5403. This oscilloscope has a capability of displaying ten characters, seven of which are utilized in the present embodiment.

That is, the Tektronix Model No. 5403 oscilloscope can display among other characters, the ten digits zero through nine, lower case letter "m" and the punctuation mark "period." The character display is determined by the current carried on two lines 701 and 703, respectively denominated "row" and "column." For the digits zero through nine, the row current is always zero, and the column current is equal to one plus the display digit multiplied by 0.1ma.

The oscilloscope under consideration provides, as control lines, ten leads, each of which is provided for one of the possible characters that the scope can display. Only seven of these leads, leads 705, 707, 709, 711, 713, 715 and 717, are shown in FIG. 7. These leads represent time slots 2, 3, 4, 5, 1, 6 and 7 respectively on the scope. The time slot 1 is reserved for the decimal point ".". Although the decimal point appears in time slot 1, by means of coding on row lead 701 and column lead 703, the decimal point can be displayed in any character position. Time slots 2 through 5, inclusive, are used for the four digits which represent the distance measured between the selected elements of the human eye. The display shows the measured distance resolved to 0.01 mm. Thus, the decimal point appears in the middle betweeen the four characters.

The remaining two time slots, slots 6 and 7, are used to display the characters "mm." As described more fully below, since the decimal point and the character "mm" are always constant, the currents needed to select these particular three characters can be generated by a fixed resistor network 759.

The interface 12 further includes a control 762 that is operable to shift the level of pulses appearing in time slot 1 (i.e., on lead 713) and to sum together the pulses in time slots 3, 4 and 5 (i.e., on leads 707, 709 and 711) and to shift the level of the resulting sum. That is, when a pulse appears on lead 713, the control 762 shifts the level thereof and produces a signal on lead 719. The pulses on leads 707-711 are summed and the resultant level thereof is shifted to produce a time slot trigger signal on lead 721.

Lead 9 from measuring section 27 provides input pulses to four-stage decade counter 723. The number of pulses provided is equal to the distance measured between the selected elements of the human eye resolved to 0.01 mm. A clear signal is provided to four-stage decade counter 723 on lead 535 from counter and control 519 in measuring section 27 (FIG. 5).

Two-stage binary counter 725 is a down counter which has its clear input connected to the lead 719 and has its clock input connected to the lead 721. Thus, two-stage binary counter 725 is reset to its initial condition at the beginning of each display cycle of numerical display 205, and counts down through its remaining three states at the leading edge of the pulses in time slots 3, 4, and 5.

Output leads 727 and 729 from two-stage binary counter 725, along with cables 731, 733, 735, and 737, each from a respective stage of the four-stage decade counter 723, apply input signals to multiplexer 739. Multiplexer 739 is responsive to the count of two-stage binary counter 725 to determine which of the four digits stored in four-stage decade counter 723 is to be displayed on numerical display 205, and routes that signal to a selected lead comprising output cable 741. That is, the contents of a stage of the counter 723 appear on the lead 741 under control of the counter 725.

The signals produced by two-stage binary counter 725 are also applied to a decoder 743 by a cable 745. Depending on the count in counter 725, decoder 743 energizes one of the leads comprising its output cable 747. Gates 749 are enabled by the signals appearing on the leads of cable 747 and are operable to route the time slot signals on leads 705-711 to output lead 751.

The signal on lead 751 is applied to BCD resistor network 753. BCD resistor network 753 provides on the output leads comprising output cable 755 the currents (i.e., 0.1, 0.2, 0.4, and 0.8 milliamperes) necessary to generate any of the desired digits.

The output cable 755 is connected to the input terminals of a gating network 757. The output terminals of the network 757 are connected to the lead 703. The gating network 757 is a conventional arrangement of gates that function to route the signal on a selected one of the leads comprising cable 755 to the output lead 703 depending upon which one of the leads comprising the cable 741 is energized. Thus, in effect, multiplexer 739 controls the operation of gating network 757.

Also connected to column lead 703 is the output lead 760 of a gated resistor network 759. Resistor network 759 is controlled by time slot leads 713, 715 and 717. As previously explained the characters displayed during those time slots remain constant in the preferred embodiment, and therefore depending upon which of those leads are activated by the standard timing circuitry of the aforementioned oscilloscope, the appropriate current is placed upon a row lead 701 and column lead 703 to display a character in that time slot.

For purposes of an example it will be assumed that the numeric display 205 is to display the distance measured of 3.00 mm.

Prior to the display, four-stage decade counter 723 will be cleared by a pulse appearing on lead 535. After a total of 64 measurment cycles, 300 pulses (representing the 3 mm distance) will appear on lead 9. These pulses will be counted and stored in four-stage decade counter 723.

At the start of a display cycle of numerical display 205, a pulse will appear in time slot 1 on lead 713. This will result in a pulse appearing on lead 719, as noted above. Since lead 719 is connected to the clear terminal CLR of counter 725, the pulse on lead 719 will clear the counter 725. By reason of the pulse on time slot 1 lead 713, the current necessary to display a decimal point will appear on row lead 701 and column lead 703.

During time slot 2, a current pulse appears on lead 705 to operate gates 749. Multiplexer 739 is responsive to the zero count in two-stage binary counter 725 and activates the leads in its output cable 741 according to the number stored in the most significant stage of four-stage decade counter 723 (i.e., a "0").

Simultaneously, decoder 743 also decodes the contents of two-stage binary counter 725 to operate gates 749 to cause the signal on lead 705 to appear on output cable 751. Gating network 757 then selects the proper leads in cable 755 from BCD resistor network 753 to put the proper signal on column lead 703 to display the proper digit in time slot 2. As previously explained the current on row lead 701 is always zero for a digit.

Similarly, the remaining digits stored in four-stage decade counter 723 (i.e., 3,0,0) are displayed sequentially in time slots 3, 4, and 5. For these three digits, the pulses in time slots 3, 4, and 5, on leads 707, 709 and 711 respectively, are summed and level-shifted by control 762 on to the lead 721. This decrements the counter with the leading edge of these time slot signals. Lastly, the two characters mm are displayed in time slots 6 and 7 under control of the current in leads 715 and 717 which generate the proper currents on row leads 701 and column lead 703 by means of resistor network 759.

OPERATION OF THE INVENTION

To better understand the operation of the invention, an example of its operation is presented below. For purposes of this example it will be assumed that the human eye is to be measured, and in particular, the distance between the anterior of the cornea and the surface of the retina is to be determined.

Before the commencement of the actual measurement of the distance, it is necessary to set the velocity compensating means with the predetermined velocity with which the trace signals pass through the elements of the eye. However, since the measurement is to be taken through a number of elements of the eye, for each of these elements (cornea, lens, etc.) an average velocity must be assumed. For ease of calculations, a velocity of 1,500 meters per second will be used. Therefore, switches 559 are manipulated to preset DRM 557 to an assumed velocity of 1,500 meters per second. Furthermore, update oscillator 529 is set by means of a variable resistor to produce a pulse once every second, thereby setting flip-flop 527, which causes counter and control 519 to update the distance measured once every second.

The eye to be measured is brought into operative relationship with signal generator 1. When the eye is axially aligned with the transducer in signal generator 1, the biometric measuring device 10 is triggered.

More specifically, oscillator 301 (FIG. 3) commences oscillating. Its output is modified by shaper 305 and divided by dividers 309 and 319. The output divider 319 is differentiated by pulse shaping network 323. The output of pulse shaping network 323 is applied to signal generator 1 and becomes the trace signal. Referring to FIG. 2, this trace or "main bang" pulse can be seen as pulse 209 on screen 203.

The pulses from shaper 305 are also applied to amplitude control 313. As previously described in conjunction with FIG. 6, on lead 11 there appears pulses of three amplitudes which are applied to display means 13 to produce scale 207.

The trace signal, appearing as pulse 209 on screen 203, begins its journey through the eye. When it impinges on an interface between two elements of the eye, part of the energy of that pulse is transmitted and part is reflected as an echo. These echoes are detected by signal generator 1 and appear as pulses 211, 213, 215, 217 and 219 (FIG. 2). Because a particular pulse 211-219 represents a signal that had to travel to an interface and return, the time between any two pulses actually is twice the time it takes the trace signal to travel the distance between the interface and the signal generator.

Since the display shown on screen 203 is in real time, it is changing continuously in accordance with the rate that pulses are being emitted by pulse shaping network 323. In the preferred embodiment this rate is 1.2 kilohertz, as noted above.

As each pulse is applied to pulse shaping network 323, a pulse is also applied by means of lead 15 to measurement gate control 25 and, in particular, to start gate delay generator 401 and stop gate delay generator 403. Accordingly, pulses appear on leads 31 and 33.

The pulses on leads 31 and 33 are summed by summing amplifier 421 and are displayed as intensified pulses 221 and 223, respectively (FIG. 2). Varying variable resistor 405 will advance or delay the position of pulse 221 in channel 202. Varying variable resistor 427 will change the width of pulse 221. Similarly, the position of pulse 223 is changed by the setting of variable resistor 407 and the width thereof is changed by varying resistor 429.

In operation, variable resistors 405, 407, 427 and 429 are adjusted so as to superimpose a pulse 221 and 223 on the appropriate echo pulses of the elements between which the distance is to be measured. Thus, in FIG. 2, pulse 221 has been superimposed over the anterior cornea echo 211 and pulse 223 has been superimposed on the retina echo 219. Under normal conditions, the pulses 221 and 223 are wider than the information pulses of interest. In other words, the pulses 211 and 213 bracket the pulses of interest. However, as noted above, the "start" pulse on lead 31 in FIG. 4 is produced in response to the leading edge of the first pulse produced by the echo from the anterior surface of the cornea (i.e., when the leading edge of the pulse is received by signal generator 1). Similarly, "stop" pulse on lead 33 occurs at the same time the leading edge of the first pulse produced by the echo signal from the surface of the retina is received by signal generator 1. These start and stop pulses are now used to control measuring section 27 to determine automatically the distance between the anterior surface of the cornea and the surface of the retina.

As shown in FIG. 5, the coincidence of a start pulse on lead 31 and an echo signal on lead 7 produces a pulse on lead 505 that sets flip-flop 509.

Assuming that this was the first "start" pulse of this particular cycle, the setting of flip-flop 509 causes counter and control 519 to count one pulse and enables gate 539 to permit pulses from oscillator 513 to pass to up/down counter 523 through divide-by-four divider 549. When a stop pulse does appear on lead 33, flip-flop 509 is reset, disabling gate 539 to prevent pulses from oscillator 513 to pass through to up/down counter 523. At this point, up/down counter 523 has recorded the number of pulses that have been generated by oscillator 513 divided by divider 549, during the time between one start and stop pulse.

Subsequently, another trace pulse is produced, causing the concomitant echoes and start and stop pulses on lead 31 and 33, respectively. Flip-flop 509 is again set and causes counter and control 519 to increment one and up/down counter 523 to count the number of pulses (divided by four) produced by oscillator 513 during the period between the start and stop pulses.

This process continues until counter and control 519 reaches a count of 64. When it reaches that count, counter and control 519 produces a convert pulse on lead 521. At this point, up/down counter 523 contains a count equal to the number of pulses from oscillator 513 divided by four, that occurred during the 64 cycles of measuring the distance between the selected elements of the eye.

The convert pulse on lead 521 conditions DRM divider 546 to permit gate 543 to pass only every fourth pulse from oscillator 513. The convert pulse on lead 521 also switches up/down counter 523 into the count down mode of operation.

Pulses from DRM divider 546 are applied both to up/down counter 523 through divider 549, causing it to count down at 1/16 the frequency of oscillator 513, and to DRM 557 at a pulse rate of one quarter the frequency of oscillator 513. DRM 557 multiplies the pulses from DRM divider 547 by the proper fraction according to the setting of BCD velocity switches 559. When up/down counter 523 decreased to zero, a borrow pulse is produced on line 555 which totally inhibits DRM divider 547 and input divider 549. As previously explained, the pulses applied to DRM 557 by oscillator 513 through divider 547 are equal to the pulses that were applied to counter 523 during the preceding 64 cycles of measuring the distance between the elements of the eye. The output of DRM 557 is further divided by divider 563 and produces pulses on lead 9 which, as previously described, are directly converted by interface 12 into signals for displaying the distance between the interfaces of the elements of the eye selected by start pulse 221 and stop pulse 223.

Using a numerical example to facilitate an understanding of the invention it is assumed that BCD velocity switches 559 are set at a value of 1500 meters per second. Further, the count stored by up/down counter 523 is divided by 4 by divider 549. Therefore, after the 64 cycles, up/down counter 523 will contain a count equal to 1600 (i.e., $$\left( \frac{6mm \times 25MHz \times 64}{1.5 \times 10^6 mm \times 4} \right)).$$

(The 6mm factor represents the round trip distance for the echo pulse. That is, the signal travels 3mm to the object and the echo travels 3mm from the object back to the transducer.) At this point, up/down counter 523 commences to count down. Since the clock frequency on lead 559 to DRM 557 is four times the count down frequency of up/down counter 523 due to input divider 549, the total number of pulses produced on lead 559 during the operation is 6400. The output pulses on lead 561 from DRM 557 is 4,800 pulses $$\left( \frac{6400 \times 1500}{2,000} \right);$$

and the number of output pulses on lead 9 to display means 13 is 300 pulses. This display shows distance with 0.01 mm resolution, and therefore display 205 will show "3.00 mm."

Where more accurate measurements are desired, the gates may be set so that the elements comprising the eye are measured sequentially, and the distance between elements is then added. That is, the velocity switches may be set for the velocity of sound in the lens. The intensified pulses are then set to be superimposed on the pulses 215 and 217 and the thickness of the lens is determined. The velocity switches are then set for the velocity of sound in the medium between the lens and the retina and a distance measurement taken. In this manner, the exact distance between desired portions of the eye may be obtained.

While the invention has been particularly shown and described with reference to a preferred embodiment, it will be understood by those skilled in the art that changes in form and details, some of which have been described, may be made without departing from the spirit and scope of the invention.

What is claimed is:

1. A biometric measuring device for measuring distances between elements in the human eye comprising:
    (a) signal generating means for producing timed sequence signals representing the distance between the elements for each cycle of operation;
    (b) converting means for converting said timed sequence signals into distance signals representing the distance between selected eye elements averaged over a predetermined number of cycles;
    (c) said converting means comprising averaging means for accumulating during said predetermined number of cycles a continuous count representative of the distance between the selected elements, dividing means for dividing said count into said averaging means by said predetermined number of cycles to produce said distance signals, and variable delay gating means selectively operable to connect the same preselected ones of said timed sequence signals to said averaging means during said predetermined number of cycles to produce distance signals representing the distance between selected eye elements; and
    (d) display means responsive to said distance signals for displaying the distance represented thereby.

2. A biometric measuring device as in claim 1, in which said display means is a numeric display.

3. A biometric measuring device as in claim 1, in which said converting means further comprises scale generator means for generating scaled graduation signals, said display means comprising screen means responsive to said timed sequence signals for visually displaying said signals, and being responsive to said scaled graduation signals for displaying said scaled graduation signals adjacent to said timed sequence signals.

4. A biometric measuring device as in claim 1, in which said converting means comprises a clock for producing clock pulses, said averaging means comprising accumulating means for accumulating the count of said clock pulses, said variable delay gating means responsive to one of said timed sequence signals corresponding to one of said selected elements for connecting said clock with said accumulating means, and responsive to another of said timed sequence signals representing another of said selected elements for disconnecting said clock therefrom.

5. A biometric measuring device as in claim 4, and control means for controlling the operation of said accumulating means for said preselected number of cycles so that said accumulating means counts the total number of clock pulses produced during said preselected number of cycles, said dividing means being operable to divide the count accumulated by said accumulating means by said predetermined number of cycles to produce said distance between signals.

6. A biometric measuring device as in claim 5, in which said accumulating means is an up/down counter.

7. A biometric measuring device as in claim 6, and a digital rate multiplier connected to said counter and responsive to said control means for multiplying the count in said counter by a preselected rate.

8. A biometric measuring device as in claim 7, in which said signal generating means comprises means for applying trace signals to the body, and said digital rate multiplier comprises a variable rate multiplier presettable to a preselected rate corresponding to the velocity of said trace signals in the body, whereby said distance signals are velocity compensated.

9. A biometric measuring device for measuring distances between selected elements in the human eye comprising signal generating means for producing timed sequence signals representing the distance between the elements for each cycle of operation; converting means for converting said timed sequence signals into distance signals representing the distance between said selected elements averaged over a predetermined number of cycles; and display means responsive to said distance signals for displaying the distance represented thereby; said signal generating means comprising trace signal generating means for applying trace signals to the body, receiving means receiving said trace signals from the body for producing said timed sequence signals in response thereto, said converting means comprising velocity compensating means for compensating for velocity differences of said trace signal in corresponding different portions of the body.

10. A biometric measuring device as in claim 9, in which said display means comprises a character display for displaying the output of said velocity compensating means as the distance measured.

11. A biometric measuring device as in claim 10, in which said display means comprises an oscilloscope having a first channel, a second channel and a character display channel, said display screen displaying the signals applied to said first, second and character display channels, means for applying said timed sequence signals to said first channel, means for applying said scaled graduation signals to said second channel to display said scale on said screen, and means for applying the output of said velocity compensating means to said character display channel.

12. A biometric measuring device for measuring distances between selected elements in the human body comprising:
    (a) a transducer for transmitting trace signals to the human body whereby said trace signals are reflected from said elements;
    (b) receiving means for converting said reflected trace signals into timed sequence signals;
    (c) converting means for converting said timed sequence signals into distance signals representing the distance between said selected elements;
    (d) said converting means comprising velocity compensating means for compensating for the difference in velocity of said trace signals in corresponding different parts of the body; and
    (e) display means responsive to said distance signals for displaying the distances represented thereby.

13. A biometric measuring device as in claim 12, in which said velocity compensating means comprises a digital rate multiplier having variable and presettable multiplying rates of said trace signals in different parts of the body.

14. A biometric measuring device for measuring distances between selected elements in the human eye comprising signal generating means for producing timed sequence signals representing the distance between the elements for each cycle of operation; converting means for converting said timed sequence signals into distance signals representing the distance between said selected elements averaged over a predetermined number of cycles; and display means responsive to said distance signals for displaying the distance represented thereby; said converting means further comprising: control means for producing a first control signal before said trace means has completed said predetermined number of cycles and a second control signal after said trace means has completed said predetermined number of cycles; a clock for generating clock pulses; clock dividing means responsive to said first control signal for transmitting said clock pulses divided by a predetermined factor; counter dividing means for dividing the output of said clock dividing means by said predetermined factor; counter means responsive to said first control signal for accumulating to its initial count the output of said counter dividing means and responsive to said second control signal for subtracting the output of said counter dividing means and for providing an initial signal when said initial count is reached; multiplier means responsive to said second control signal and said initial signal for multiplying the output of said clock dividing means by a predetermined rate between the reception of said second control signal and said initial signal.

* * * * *